(12) United States Patent
Kida

(10) Patent No.: US 12,082,966 B2
(45) Date of Patent: Sep. 10, 2024

(54) RADIATION IMAGING APPARATUS AND RADIATION IMAGING SYSTEM

(71) Applicant: CANON KABUSHIKI KAISHA, Tokyo (JP)

(72) Inventor: Akira Kida, Kanagawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 56 days.

(21) Appl. No.: 17/708,256

(22) Filed: Mar. 30, 2022

(65) Prior Publication Data
US 2022/0313193 A1    Oct. 6, 2022

(30) Foreign Application Priority Data

Mar. 30, 2021 (JP) ................. 2021-058314

(51) Int. Cl.
*A61B 6/00* (2024.01)
*A61B 6/10* (2006.01)

(52) U.S. Cl.
CPC ............ *A61B 6/5211* (2013.01); *A61B 6/107* (2013.01); *A61B 6/4405* (2013.01)

(58) Field of Classification Search
CPC ..... A61B 6/4405; A61B 6/4283; A61B 6/107; A61B 6/4233; A61B 6/44; A61B 6/461; A61B 6/5211
See application file for complete search history.

(56) References Cited

U.S. PATENT DOCUMENTS

| | | | |
|---|---|---|---|
| 9,968,315 B2 | 5/2018 | Ogura et al. | |
| 2010/0111263 A1* | 5/2010 | Lamberty | A61B 6/4283 378/189 |
| 2010/0148081 A1* | 6/2010 | Yoshimi | A61B 6/4233 250/370.08 |
| 2010/0284521 A1* | 11/2010 | McBroom | A61B 6/4233 378/204 |
| 2011/0069814 A1* | 3/2011 | Yonekawa | A61B 6/4283 378/62 |
| 2011/0222657 A1* | 9/2011 | Kobayashi | A61B 6/56 378/62 |
| 2012/0153172 A1* | 6/2012 | Sumi | A61B 6/44 250/369 |

(Continued)

FOREIGN PATENT DOCUMENTS

JP    2016-63875 A    4/2016
JP    2017-53821 A    3/2017

*Primary Examiner* — Dani Fox
*Assistant Examiner* — Soorena Kefayati
(74) *Attorney, Agent, or Firm* — VENABLE LLP

(57) ABSTRACT

Provided is a radiation imaging apparatus, comprising: a radiation detection panel configured to detect incident radiation and convert the detected incident radiation into an electric signal; a housing including the radiation detection panel and having a front surface into which the radiation is incident, a back surface at a position opposed to the front surface, and a side surface positioned between the front surface and the back surface; and a light source included in the housing, configured to emit light indicating a state of the radiation imaging apparatus, wherein the light source is arranged inside the outer shape of the radiation detection panel, obtained by projecting the radiation detection panel onto the back surface.

19 Claims, 9 Drawing Sheets

(56) References Cited

U.S. PATENT DOCUMENTS

| | | | |
|---|---|---|---|
| 2013/0136235 A1* | 5/2013 | Liu | A61B 6/56 250/394 |
| 2013/0259208 A1* | 10/2013 | Watanabe | A61B 6/4283 378/182 |
| 2015/0253441 A1* | 9/2015 | Horiuchi | A61B 6/4283 250/361 R |
| 2015/0293239 A1* | 10/2015 | Miyoshi | G01T 7/00 250/394 |
| 2016/0081638 A1* | 3/2016 | Ogura | A61B 6/4283 378/185 |
| 2016/0089092 A1* | 3/2016 | Shimizukawa | A61B 6/44 378/98 |
| 2017/0090044 A1* | 3/2017 | Suzuki | A61B 6/4283 |
| 2018/0092618 A1* | 4/2018 | Tagawa | A61B 6/40 |
| 2019/0046139 A1* | 2/2019 | Hattori | A61B 6/563 |
| 2019/0293812 A1* | 9/2019 | Suzuki | G01T 7/00 |

* cited by examiner

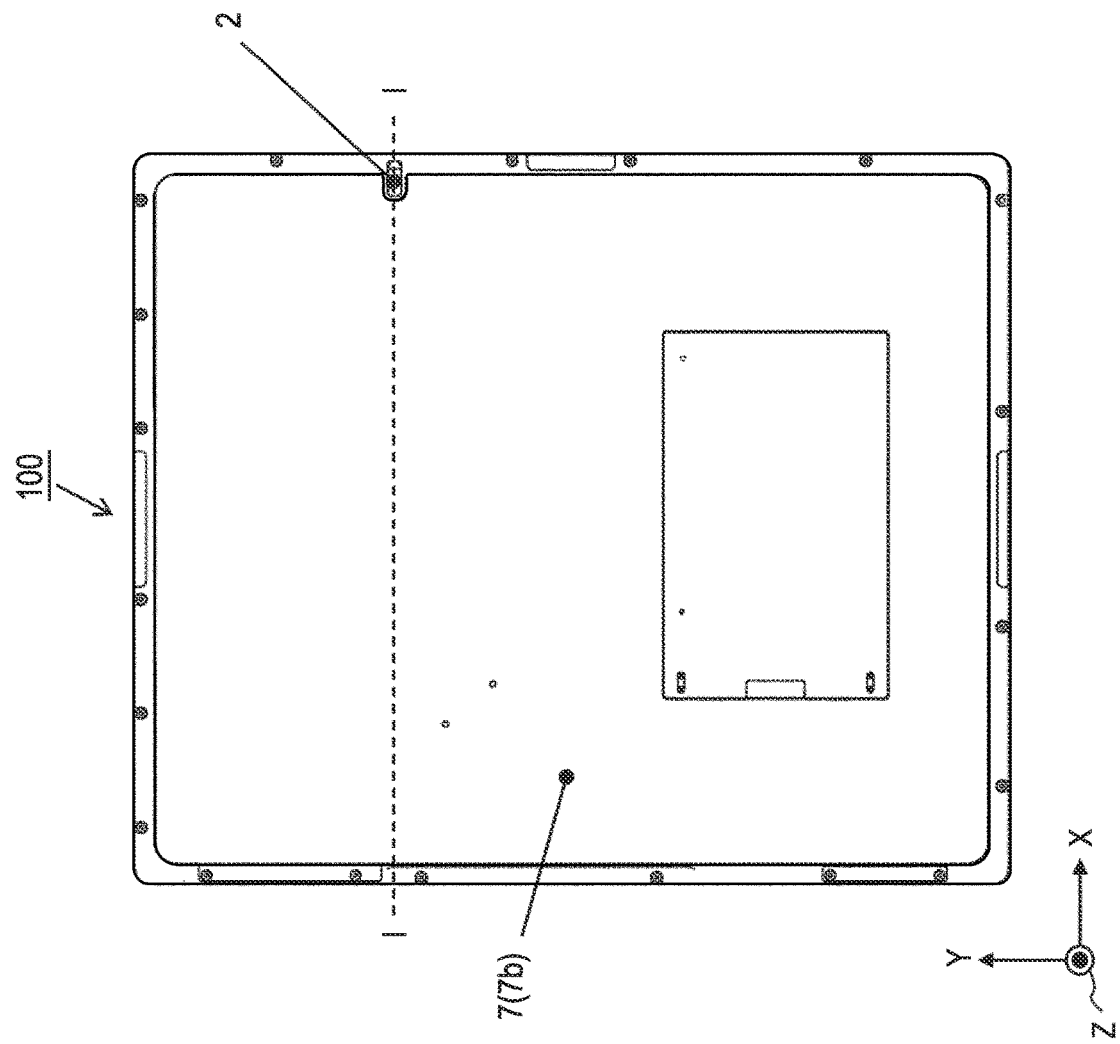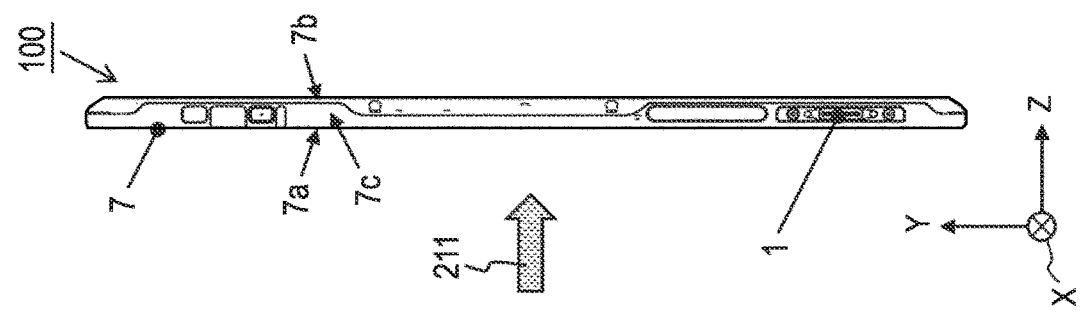

RADIATION IMAGING APPARATUS AND RADIATION IMAGING SYSTEM

BACKGROUND OF THE INVENTION

Field of the Invention

The present invention relates to a radiation imaging apparatus for detecting incident radiation and acquiring a radiation image, and a radiation imaging system including the radiation imaging apparatus.

Description of the Related Art

The radiation imaging apparatus that irradiates an object with radiation and acquires a radiation image of the object by detecting the intensity distribution of the radiation transmitted through the object is widely used in nondestructive inspection for industrial purpose and medical diagnosis. In recent years, a digital radiation imaging apparatus having a radiation detection panel for imaging a digital radiation image is used.

A thin, lightweight, portable type radiation imaging apparatus that enables rapid and wide-area imaging is called an electric cassette. After the electric cassette is inserted into a platform or a recumbent, it is carried to another platform or a recumbent and can be continuously used for imaging.

Japanese Patent Application Laid-Open No. 2016-63875 discloses an electric cassette provided with a light source for emitting light according to an operation state of the electric cassette, the light source being positioned toward a display window provided on an inclined plane formed between a side surface and a bottom surface of a housing.

Japanese Patent Application Laid-Open No. 2017-53821 discloses a radiation imaging apparatus in which a light source for emitting light indicative of a communication state is provided on a display portion disposed on a side surface of a housing.

In any of the conventional radiation imaging apparatuses described above, a light source that emits light indicative of the state of the radiation imaging apparatus is disposed between the radiation detection panel and the side surface of the housing so that the state of the radiation imaging apparatus can be viewed from the side surface direction of the housing. Therefore, the frame size of the housing becomes considerably larger than the size of the radiation detection panel, and as a result, there is a problem that the weight of the entire radiation imaging apparatus increases and the portability of the radiation imaging apparatus deteriorates.

Further, a means for easily confirming whether or not the electric cassette is properly connected to the platform or the like, when the electric cassette is inserted into a platform or the like, is required. In particular, since the connection terminals of the platform or the recumbent are often disposed at the back of the insertion portion, it is desirable that the above described means be disposed on the side opposite to the side surface on which the connection terminals are disposed in the electric cassette.

SUMMARY OF THE INVENTION

The present disclosure has been made in view of such a circumstance, and it is an object of the present disclosure to provide a mechanism for visually confirming a state of a radiation imaging apparatus while suppressing an increase in a size of a frame of a housing.

The disclosed radiation imaging apparatus comprises: a radiation detection panel configured to detect incident radiation and convert the detected incident radiation into an electric signal; a housing including the radiation detection panel and having a front surface into which the radiation is incident, a back surface at a position opposed to the front surface, and a side surface positioned between the front surface and the back surface; and a light source included in the housing, configured to emit light indicating a state of the radiation imaging apparatus, wherein the light source is arranged inside an outer shape of the radiation detection panel, obtained by projecting the radiation detection panel onto the back surface.

The present invention also includes a radiation imaging system comprising the radiation imaging apparatus described above.

Further features of the present invention will become apparent from the following description of exemplary embodiments with reference to the attached drawings.

BRIEF DESCRIPTION OF THE DRAWINGS

FIG. 2A is a side view showing an example of the external configuration of the radiation imaging apparatus according to the first embodiment.

FIG. 2B is a plane view showing an example of the external configuration of the radiation imaging apparatus according to the first embodiment.

FIG. 6 is a perspective view of the light guide lens disposed between the back frames of FIG. 5 as seen from the front side of the housing without the control substrate or the like.

DESCRIPTION OF THE EMBODIMENTS

Embodiments of the present disclosure will be described below with reference to the drawings. It should be noted that the dimensions and structures of the various structures in the embodiments of the present disclosure described below are not limited to those shown in the description and drawings.

First Embodiment

First, a first embodiment of the present disclosure will be described.

<Schematic Configuration of Radiation Imaging System>

Figure 1:
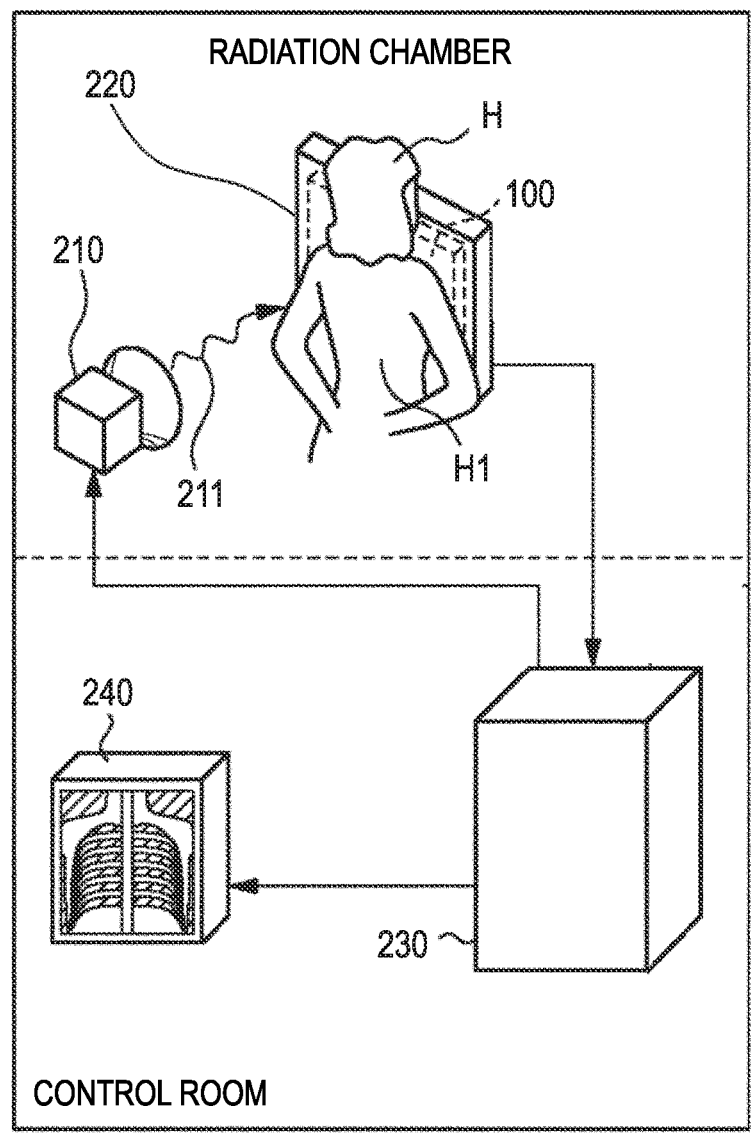
FIG. 1 is a schematic diagram showing an example of the schematic configuration of a radiation imaging system according to the first embodiment.

FIG. 1 shows an example of a schematic configuration of a radiation imaging system 10 according to a first embodiment of the present disclosure. The radiation imaging system 10 includes a radiation imaging apparatus 100, a radiation source 210, a platform 220, a signal processing apparatus 230, and a display apparatus 240. In the example of the radiation imaging system 10 shown in FIG. 1, the radiation imaging apparatus 100, the radiation source 210, and the platform 220 are installed in the radiation chamber, and the signal processing apparatus 230 and the display apparatus 240 are installed in the control room.

The radiation imaging apparatus 100 is an apparatus for performing imaging using the radiation 211. The radiation imaging apparatus 100 is inserted into the platform 220 and held near the imaged position H1 of the object H, such as a patient. The radiation source 210, which is a radiation generating apparatus, irradiates radiation 211 toward the imaged position H1 of the object H under the control of the signal processing apparatus 230. The radiation 211 transmitted through the imaged position H1 of the object H enters the radiation imaging apparatus 100. The radiation imaging apparatus 100 detects the incident radiation 211 as an electric signal related to the radiation image, converts it into a digital electric signal, and outputs it to the signal processing apparatus 230. In the signal processing apparatus 230, an electric signal outputted from the radiation imaging apparatus 100 is subjected to image processing to generate a radiation image (image data), which is outputted to the display apparatus 240. The display apparatus 240 displays the radiation image output from the signal processing apparatus 230 so that the examinee or the like can confirm (visually recognize) the radiation image at the imaged position H1 of the object H, which is the object.

<Schematic Configuration of Radiation Imaging Apparatus>

FIGS. 2A and 2B show an example of the external configuration of the radiation imaging apparatus 100 according to the first embodiment of the present disclosure, and the same reference numerals are given to the same configuration as that shown in FIG. 1.

FIG. 2A is a view of the radiation imaging apparatus 100 as viewed from the side surface 7c of the housing 7. The radiation imaging apparatus 100 includes a housing 7. The housing 7 includes a front surface 7a into which radiation 211 shown in FIG. 1 enters, a back surface 7b at a position facing the front surface 7a (a position opposite to the front surface 7a), and a side surface 7c located between the front surface 7a and the back surface 7b. FIG. 2A shows an XYZ coordinate system in which the incident direction of the radiation 211 is defined as the Z direction, and the two directions orthogonal to the Z direction and defining the front surface 7a or the back surface 7b of the housing 7 are defined as the X and Y directions. The side surface 7c of the housing 7 is provided with a connector 1 which can be electrically connected to the connection terminal of the platform 220. When the radiation imaging apparatus 100 is inserted into the platform 220 of FIG. 1, the connector 1 is electrically connected to the connection terminal of the platform 220, so that the radiation imaging apparatus 100 can communicate with the signal processing apparatus 230 of FIG. 1.

FIG. 2B is a view of the radiation imaging apparatus 100 as viewed from the back surface 7b of the housing 7. FIG. 2B illustrates an XYZ coordinate system corresponding to the XYZ coordinate system shown in FIG. 2A. Further, on the side of the back surface 7b of the housing 7, there is provided a light emitting portion 2 that emits light indicating the state of the radiation imaging apparatus 100. In this embodiment, when the radiation imaging apparatus 100 is inserted into the platform 220 of FIG. 1 and the radiation imaging apparatus 100 can communicate with the signal processing apparatus 230 of FIG. 1, the light emitting portion 2 emits light. In this case, the examiner or the like can recognize whether or not the radiation imaging apparatus 100 has established communication with the signal processing apparatus 230 or the like by visually confirming the presence or absence of light emission by the light emitting portion 2.

When the radiation imaging apparatus 100 is inserted into the platform 220 shown in FIG. 1, the connector 1 is inserted toward the connection terminal of the platform 220. For this reason, it is preferable from the viewpoint of visibility to arrange the light emitting portion 2 on the near side as viewed from the examiner or the like. That is, it is preferable that at least one light emitting portion 2 is arranged at a position visible from the opposite side of the side surface 7c on which the connector 1 is provided. In the present embodiment, the position where the light emitting portion 2 is disposed is not limited to the position described here, and can be applied even if the light emitting portion 2 is disposed at another position.

Figure 3:
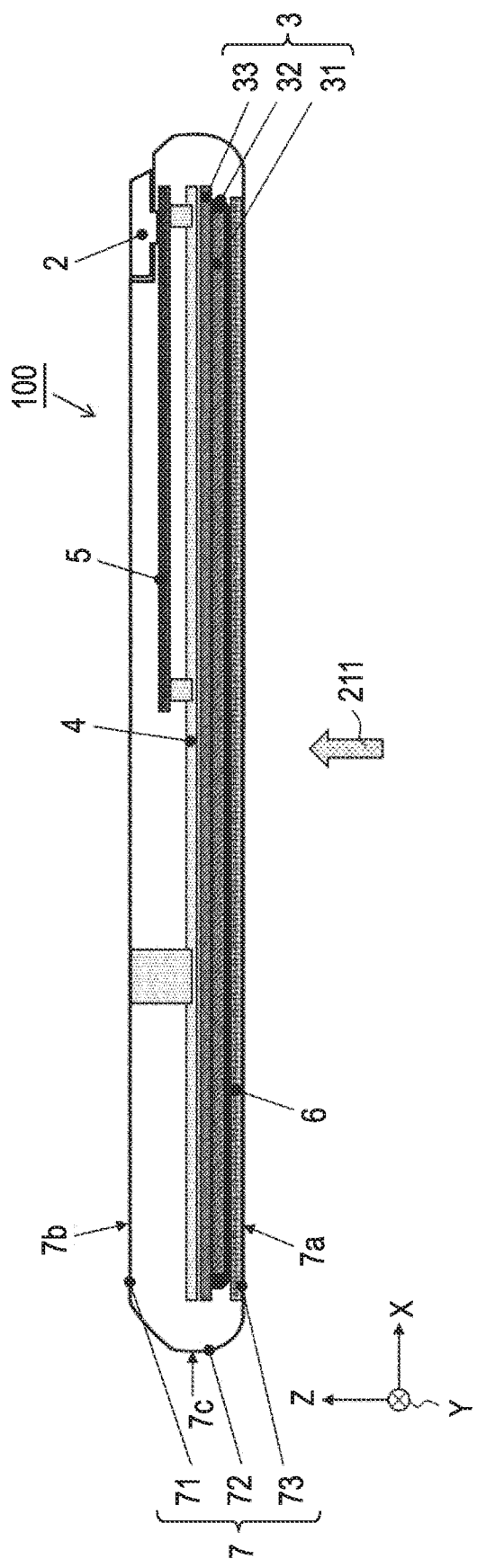
FIG. 3 is a cross-sectional view showing an example of an internal configuration in the I-I cross section shown in FIG. 2B of the radiation imaging apparatus according to the first embodiment.

FIG. 3 is a diagram showing an example of the internal configuration of the radiation imaging apparatus 100 according to the first embodiment of the present disclosure in the I-I cross section shown in FIG. 2B. In FIG. 3, components similar to those shown in FIGS. 2A and 2B are denoted by the same reference numerals, and a detailed description thereof will be omitted. FIG. 3 shows an XYZ coordinate system corresponding to the XYZ coordinate system shown in FIGS. 2A and 2B.

In addition to the connector 1 shown in FIG. 2A, the radiation imaging apparatus 100 includes a light emitting portion 2, a radiation detection panel 3, a support base 4, a control substrate 5, a buffer material 6, and a housing 7.

The radiation detection panel 3 detects incident radiation 211 as an electric signal related to a radiation image. In this embodiment, the radiation detection panel 3 includes a fluorescence material layer (scintillator layer) 31, a fluorescence material protective film 32, and a sensor substrate 33.

The fluorescence material layer 31 converts incident radiation 211 into light. The fluorescence material protective film 32 is formed so as to cover the fluorescence material layer 31 so as to protect the fluorescence material layer 31, and is made of, for example, a material having low moisture permeability. The sensor substrate 33 is formed by arranging a large number of photoelectric conversion elements (sensors) on the upper portion thereof for converting light generated in the fluorescence material layer 31 into electric charges that are electric signals.

The radiation detection panel 3 of this embodiment is an indirect conversion type radiation detection panel that converts incident radiation 211 into light by the fluorescence material layer 31, converts the light into electric charge by the photoelectric conversion element of the sensor substrate 33, and finally outputs the electric signal related to the radiation image.

The support base 4 supports the radiation detection panel 3 from the side of the back surface 7b of the housing 7. The support base 4 is made of a material having high rigidity in order to prevent the radiation detection panel 3 from being bent or broken.

The control substrate 5 is an electric substrate arranged so as to be placed on the support base 4 on the side of the back surface 7b of the housing 7 rather than the support base 4. The control substrate 5 controls the operation of the radiation detection panel 3, and controls light emission by the light emitting portion 2, and the like.

The buffer material 6 is disposed between the front surface 7a (more specifically, a top cover 73 to be described later) of the housing 7 and the radiation detection panel 3, and has a function of protecting the radiation detection panel 3 from an external impact.

The housing 7 is an exterior casing including the radiation detection panel 3, the support base 4, the control substrate 5, and the buffer material 6. In this embodiment, the housing 7 includes a back cover 71 formed on the back surface 7b, a frame 72 formed in an area including the side surface 7c (which may include a part of the back surface 7b), and a top cover 73 formed on the front surface 7a.

Figure 4:
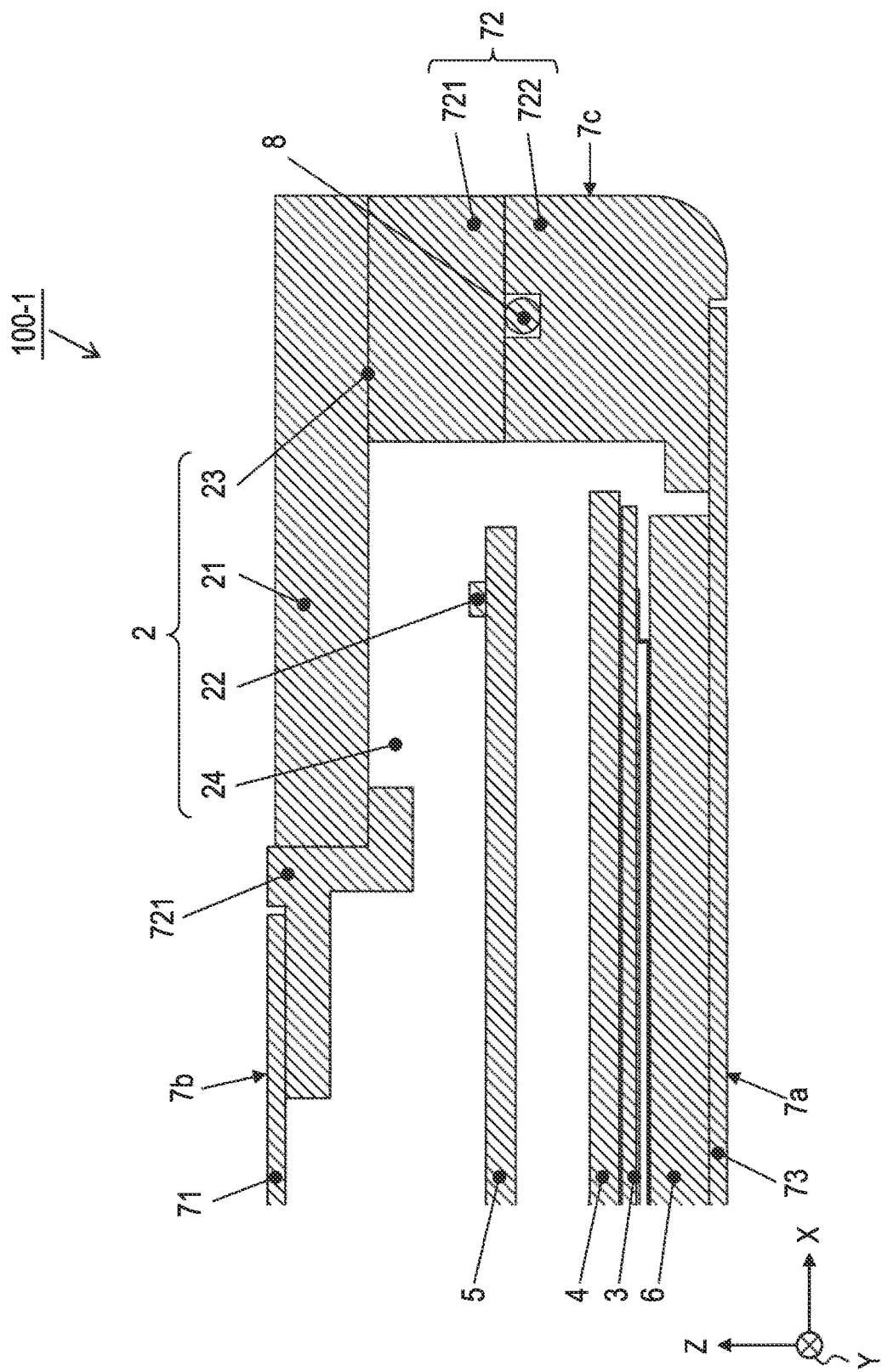
FIG. 4 is an enlarged view showing a detailed structural example of the vicinity of the light emitting portion of FIG. 3 in the radiation imaging apparatus according to the first embodiment.

FIG. 4 shows a radiation imaging apparatus 100 according to the first embodiment of the present disclosure, and shows a detailed example of the structure near the light emitting portion 2 of FIG. 3. In FIG. 4, components similar to those shown in FIG. 3 are denoted by the same reference numerals, and a detailed description thereof will be omitted. FIG. 4 shows an XYZ coordinate system corresponding to the XYZ coordinate system shown in FIG. 3. In the following description, the radiation imaging apparatus 100 according to the first embodiment shown in FIG. 4 is described as "radiation imaging apparatus 100-1".

In the radiation imaging apparatus 100-1 shown in FIG. 4, the frame 72 of the housing 7 shown in FIG. 3 is divided into a part of the back frame 721 positioned on the side of the back surface 7b of the housing 7 and a part of the front frame 722 positioned on the side of the front surface 7a of the housing 7. Further, the back frame 721 is divided into a part in contact with the front frame 722 formed on the side surface 7c and a part in contact with the back cover 71 formed on the back surface 7b. In this embodiment, the frame 72 of the housing 7 does not necessarily have to be composed of a plurality of components.

A waterproof rubber 8 is provided between the back frame 721 and the front frame 722 so as to ensure the waterproofness of the housing 7.

The light emitting portion 2 shown in FIGS. 2A and 3 includes a light guide lens 21, an LED light source 22, a first surface 23, and an opening 24. The light guide lens 21 is a transparent member (including a translucent member) that receives light emitted from the LED light source 22. The LED light source 22 is included in the housing 7 and arranged on the side of the back surface 7b of the housing 7 in the control substrate 5. The LED light source 22 is electrically connected to the control substrate 5, and is a light source that emits light indicative of the state of the radiation imaging apparatus 100-1 (emits light according to the state of the radiation imaging apparatus 100-1) based on the control of the control substrate 5. In this embodiment, the LED light source 22 emits light indicating a state of connection with the platform 220 (or a recumbent not shown) of FIG. 1 into which the radiation imaging apparatus 100-1 is inserted, and emits light, for example, when the radiation imaging apparatus 100-1 is electrically connected with the platform 220 (or the recumbent not shown) of FIG. 1. The first surface 23 is a surface substantially parallel to the back surface 7b of the housing 7 and extending to the edge in the frame 72 of the housing 7 formed in a region including the side surface 7c of the housing 7, and at least a part of the region is a surface in contact with the light guide lens 21 composed of a transparent member. The opening 24 is an opening provided in the vicinity of the first surface 23. The opening 24 is an opening formed between a part of the back frame 721 in contact with a front frame 722 formed on a side surface 7c and a part of the back frame 721 in contact with a back cover 71 formed on a back surface 7b. A light guide lens 21 is mounted on the opening 24.

The light emitted from the LED light source 22, as described above is emitted to the outside of the housing 7 through the opening 24.

Further, the light emitted from the LED light source 22, as described above is diffused from the direction toward the back surface 7b of the housing 7 to the direction toward the side surface 7c of the housing 7 through the light guide lens 21 (opening 24).

By visually recognizing the light guided in the direction toward the side surface 7c of the housing 7, the examiner or the like can recognize that the radiation imaging apparatus 100-1 is electrically connected to the platform 220 (or the recumbent, not shown) and communication between the radiation imaging apparatus 100-1 and the signal processing apparatus 230 or the like has been established. That is, the state of the radiation imaging apparatus 100-1 includes a state in which the radiation imaging apparatus 100-1 is inserted into the platform 220 and can communicate with the signal processing apparatus 230, and a state in which the radiation imaging apparatus 100-1 is inserted into the platform 220 but cannot communicate with the signal processing apparatus 230.

Although the LED light source 22 is used in the present embodiment, another light source may be used instead of the LED as long as the light source can be placed on the control substrate 5. Further, in the present embodiment, the LED light source 22 emits light when the radiation imaging apparatus 100-1 is electrically connected to the platform 220 (or the recumbent, not shown). However, for example, the LED light source may emit light when applying the power from the platform 220, a charging device, or the like is started.

When the radiation imaging apparatus 100 is inserted into the platform 220, the front surface 7a and the back surface 7b of the housing 7 are covered and cannot be seen, and therefore, it is desirable that the light emitted from the LED light source 22 is visible from the direction of the side surface 7c of the housing 7. Further, as described above, since portability is required for the radiation imaging apparatus 100, it is desirable that the outer shape (frame size) of the housing 7 including the radiation detection panel 3, the size of which is within a range capable of imaging, is not as large as possible than the size of the radiation detection panel 3. However, for example, when the opening 24 and the LED light source 22 are arranged on the side surface 7c of the housing 7, it is necessary to arrange an electric substrate for causing to emit and holding the LED light source 22 on the side surface 7c of the housing 7. In this case, the frame size of the housing 7 is considerably larger than the size of the radiation detection panel 3, and as a result, the weight of the entire radiation imaging apparatus increases and the portability of the radiation imaging apparatus deteriorates. Therefore, in the radiation imaging apparatus 100-1 according to the first embodiment, the LED light source 22 is arranged inside the outer shape (XY plane) obtained by projecting the radiation detection panel 3 onto the plane of the back surface 7b of the housing 7. In this embodiment, the LED light source 22 is arranged on the side of the back surface 7b of the housing 7 in the control substrate 5, an opening 24 is provided near the first surface 23, and light from the LED light source 22 is emitted to the outside of the housing 7 using the opening 24 and the light guide lens 21.

A waterproof rubber 8 is often disposed on the side surface 7c of the housing 7, and it is difficult to provide an opening 24 on the side surface 7c of the housing 7. Therefore, in the present embodiment, by providing the opening 24 in the back surface 7b of the housing 7, it is possible to display the connection state between the radiation imaging apparatus 100-1 and the connection terminal of the platform 220 (or the recumbent not shown) while maintaining the waterproofness.

For fixing the light guide lens 21 and the back frame 721, fixing by insertion or fixing by an adhesive can be used, and further, fixing by the waterproof double-sided tape 9 of FIG. 5 described later may be used.

In the radiation imaging apparatus 100-1 according to the first embodiment described above, the LED light source 22 emitting light indicative of the state of the radiation imaging apparatus 100 is arranged inside the outer shape obtained by projecting the radiation detection panel 3 to a plane onto the back surface 7b of the housing 7.

Second Embodiment

Next, a second embodiment of the present disclosure will be described. In the description of the second embodiment described below, the description of matters common to the first embodiment will be omitted, and matters different from the first embodiment will be described.

The schematic configuration of the radiation imaging system according to the second embodiment is the same as that of the radiation imaging system 10 according to the first embodiment shown in FIG. 1. The external appearance of the radiation imaging apparatus 100 according to the second embodiment is almost the same as that of the radiation imaging apparatus 100 according to the first embodiment shown in FIGS. 2A and 2B. Furthermore, the internal configuration of the radiation imaging apparatus 100 according to the second embodiment is almost the same as that of the radiation imaging apparatus 100 according to the first embodiment shown in FIG. 3.

Figure 5:
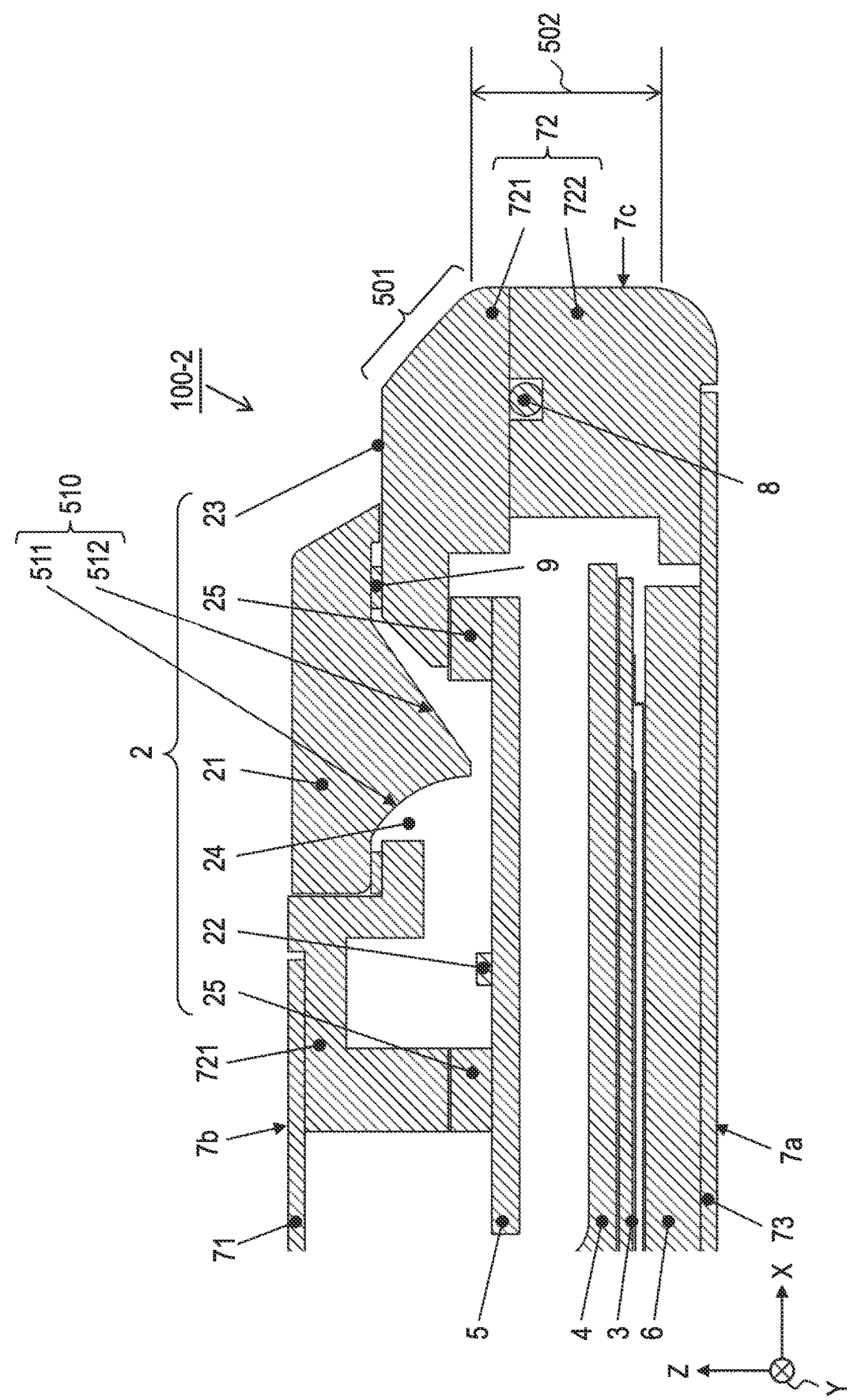
FIG. 5 is an enlarged view showing a detailed structural example of the vicinity of the light emitting portion of FIG. 3 in the radiation imaging apparatus according to the second embodiment.

FIG. 5 shows a radiation imaging apparatus 100 according to the second embodiment of the present disclosure, and shows a detailed example of the structure near the light emitting portion 2 of FIG. 3. In FIG. 5, components similar to those shown in FIGS. 3 and 4 are denoted by the same reference numerals, and a detailed description thereof will be omitted. FIG. 5 shows an XYZ coordinate system corresponding to the XYZ coordinate system shown in FIGS. 3 and 4. In the following description, the radiation imaging apparatus 100 according to the second embodiment shown in FIG. 5 is described as "radiation imaging apparatus 100-2".

In the radiation imaging apparatus 100-2, the frame 72 of the housing 7 shown in FIG. 3 is divided into a part of the back frame 721 positioned on the side of the back surface 7b of the housing 7 and a part of the front frame 722 positioned on the side of the front surface 7a of the housing 7. Further, the back frame 721 is divided into a part in contact with the front frame 722 formed on the side surface 7c and a part in contact with the back cover 71 formed on the back surface 7b. In this embodiment, the frame 72 of the housing 7 does not necessarily have to be composed of a plurality of components.

As in FIG. 4, a waterproof rubber 8 is provided between the back frame 721 and the front frame 722 to ensure the waterproofness of the housing 7. Further, a waterproof double-sided tape 9 is interposed between the light guide lens 21 and the back frame 721 to fix both.

The light emitting portion 2 shown in FIGS. 2A and 3 includes a light guide lens 21, an LED light source 22, a first surface 23, an opening 24, and a light shielding elastic member 25. Of these, the light guide lens 21, the LED light source 22, the first surface 23, and the opening 24 are the same as those of the radiation imaging apparatus 100-1 according to the first embodiment shown in FIG. 4, and therefore a detailed description thereof will be omitted. The light shielding elastic member 25 is an elastic body having light shielding property interposed between the control substrate 5 which is an electric substrate and the housing 7. In the radiation imaging apparatus 100-2 according to the second embodiment, the LED light source 22 is arranged in a space surrounded by the light guide lens 21 composed of a transparent member, the control substrate 5, the light shielding elastic member 25, and the housing 7.

In the present embodiment, the frame 72 (back frame 721) of the housing 7 has an inclined surface 501 in contact with the side surface 7c of the housing 7. In this embodiment, the light guide lens 21 is disposed inside the housing 7 more than the inclined surface 501 of the back frame 721. It is assumed that the radiation imaging apparatus 100-2 is removed from the platform 220 and carried to another platform, recumbent, or patient's room for use. In this process, it is also assumed that the housing 7 may collide with the platform 220, or the housing 7 may fall. In this case, there is a possibility that the light guide lens 21 is damaged and the light emission state of the LED light source 22 is difficult to be visually confirmed. In particular, when the housing 7 is dropped with the side surface 7c facing down, as compared with the case where the housing 7 is dropped with the back surface 7b facing down, the housing 7 receives the impact of the drop in a narrow area, and is liable to be damaged. It may also be assumed that the radiation imaging apparatus 100-2 is not only inserted into the platform 220 or the recumbent (not shown) but also directly inserted between the body of the patient lying on the bed and the bed. At this time, the joint from the side surface 7c of the housing 7 to the front surface 7a and the joint from the side surface 7c to the back surface 7b of the housing 7 can be easily inserted if they are inclined or curved, and the burden on the patient is small. When the thickness 502 of the side surface 7c of the housing 7 in the direction from the front surface 7a to the back surface 7b of the housing 7 is small, the burden on the patient at the time of insertion is similarly small. In this embodiment, in view of the above, the light guide lens 21 is disposed inside the housing 7 from the side surface 7c of the housing 7 and the inclined surface 501, thereby ensuring the impact resistance from the lateral direction. Further, by separating the light guide lens 21 from the side surface 7c of the housing 7, the thickness 502 of the side surface 7c of the housing 7 can be reduced, thereby reducing the burden on the patient.

In the present embodiment, the light guide lens 21 is formed with a projection 510 that protrudes from the opening 24 to the inside of the housing 7. The projection 510 of the light guide lens 21 has a light receiving surface 511 and a reflecting surface 512. The light receiving surface 511 faces the LED light source 22 and receives light emitted from the LED light source 22.

The reflecting surface 512 is opposed to the light receiving surface 511 and reflects light incident on the light guide lens 21 from the light receiving surface 511 (light arriving from the light receiving surface 511). In this case, in the present embodiment, the light receiving surface 511 is shaped to be recessed toward the inside of the light guide lens 21. Since the light incident on the recessed surface of the lens is diffused at an angle wider than that at the time of incidence, the light passing through the light receiving surface 511 is diffused over a wider range. The reflecting surface 512 reflects light intended to be emitted from the light guide lens 21 to the inside of the housing 7 again and directs it to the outside direction of the housing 7. With such a configuration, the visibility of the light emitting portion 2 can be improved.

Further, the light receiving surface 511 of the light guide lens 21 has an arc shape, and in the present embodiment, the radius of the arc is smaller than the distance between the light receiving surface 511 and the LED light source 22.

Figure 6:
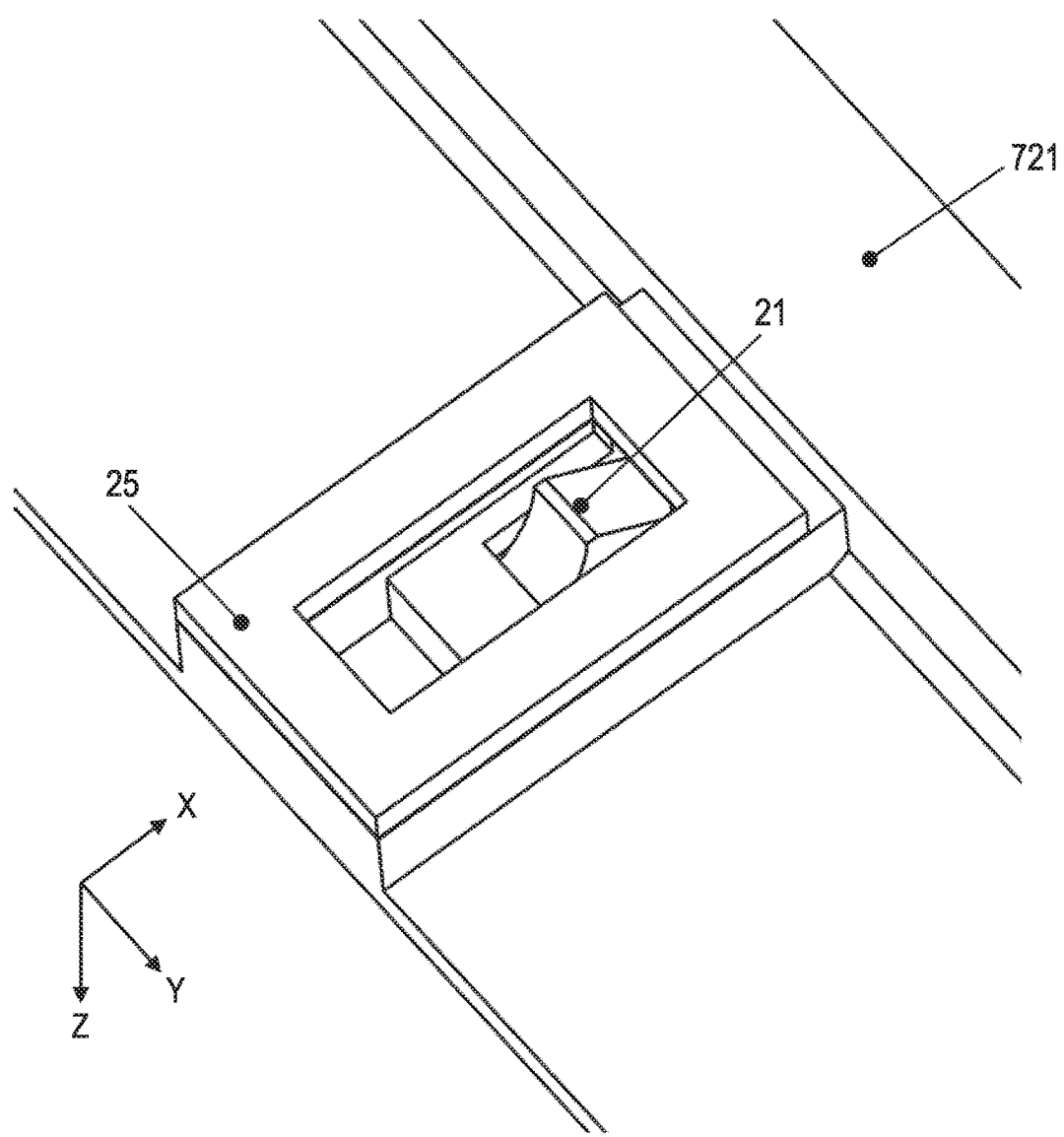

FIG. 6 shows a second embodiment of the present invention, in which the light guide lens 21 disposed between the back frames 721 in FIG. 5 is viewed from the front surface 7a of the housing 7 without showing the control substrate 5 and the like. In FIG. 6, components similar to those shown in FIG. 5 are denoted by the same reference numerals, and a detailed description thereof will be omitted. FIG. 6 shows an XYZ coordinate system corresponding to the XYZ coordinate system shown in FIG. 5.

In this embodiment, it is desirable that the light emitted from the LED light source 22 does not reach the radiation detection panel 3. This is because the radiation detection panel 3 converts the radiation 211 into light and captures it as an electric signal related to the radiation image, so that when the light from the LED light source 22 arrives, the light from the LED light source 22 may be imaged in the radiation image, to occur a misdiagnosis. In this embodiment, as described above, the LED light source 22 is disposed in a closed space surrounded by the control substrate 5, the light shielding elastic member 25, the housing 7, and the light guide lens 21. Thus, the light emitted from the LED light source 22 does not leave the space except for the light guide lens 21. In general, however, the glass epoxy resin used as the material of the electric substrate related to the control substrate 5 is not necessarily capable of completely shielding light. Therefore, it is desirable that the control substrate 5 is configured to be prevented from transmitting light at least in the region inside the projection of the light shielding elastic member 25.

Therefore, in the control substrate 5, a pattern of a copper foil layer as a light shielding layer for blocking light emitted from the LED light source 22 from transmitting to the side of the radiation detection panel 3 is formed without a gap in an inside of a region obtained by the projecting the light shielding elastic member 25.

By adopting this configuration, it is possible to prevent the light emitted from the LED light source 22 from reaching the radiation detection panel 3. It should be noted that the configuration in which the pattern of the copper foil layer serving as the light shielding layer is formed on the control substrate 5 is also applicable to the control substrate 5 of the radiation imaging apparatus 100-1 according to the first embodiment described above.

Figure 7:
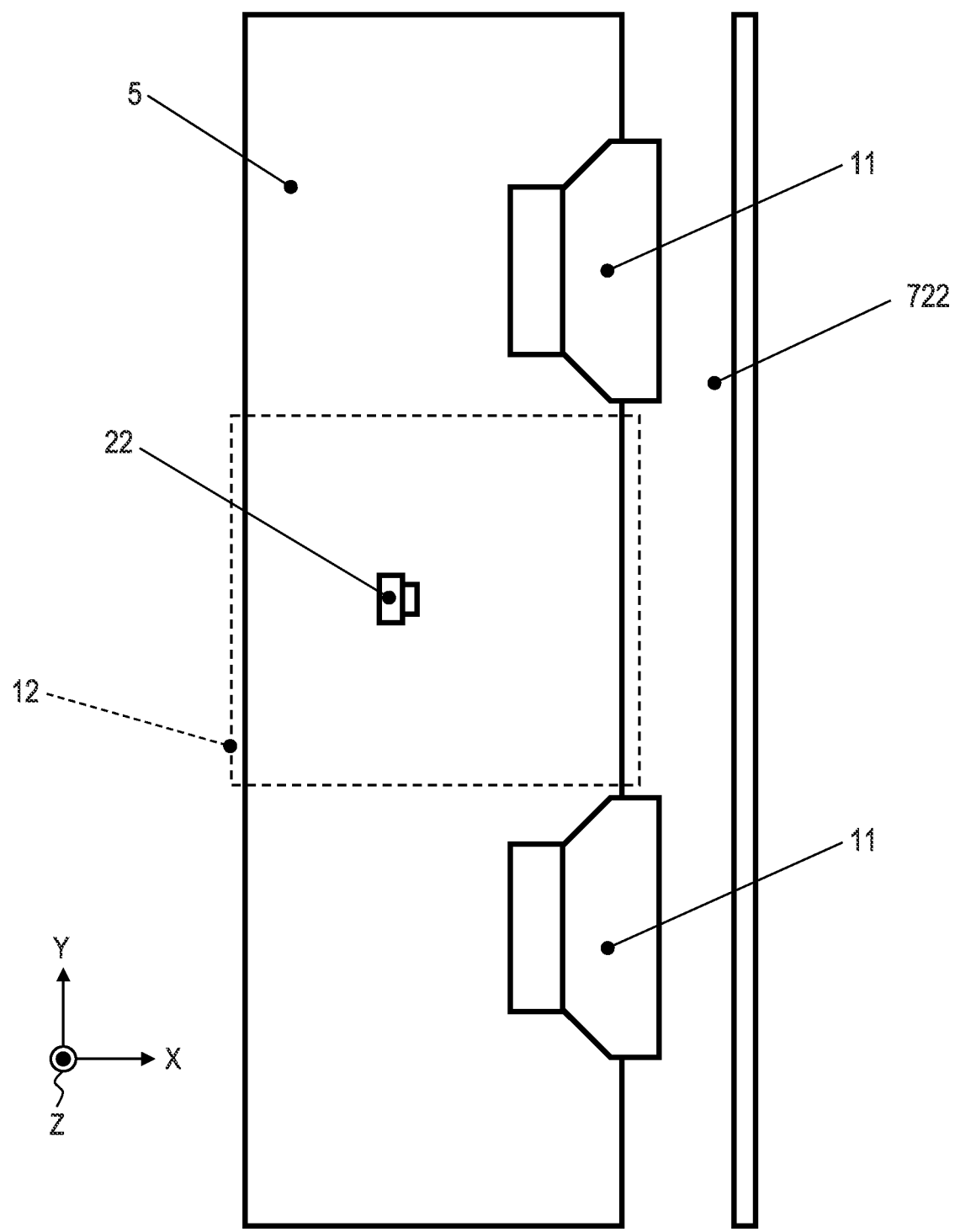
FIG. 7 is a plan view of the LED light source, control board and the like of FIG. 5 as viewed from the back side of the housing in the second embodiment.

FIG. 7 shows the second embodiment of the present invention, in which the LED light source 22, the control substrate 5, and the like of FIG. 5 are viewed from the side of the back surface 7b of the housing 7. In FIG. 7, components similar to those shown in FIG. 5 are denoted by the same reference numerals, and a detailed description thereof will be omitted. FIG. 7 shows an XYZ coordinate system corresponding to the XYZ coordinate system shown in FIG. 5.

The plurality of flexible substrates 11 are included in the housing 7 and are substrates for electrically connecting the control substrate 5 and the radiation detection panel 3. In order to avoid interference with the internal components of the connector 1, the flexible substrate 11 is generally disposed on the side surface 7c opposite to the side surface 7c of the housing 7 in which the connector 1 is disposed. That is, in this embodiment, the flexible substrate 11 is disposed on the same side surface 7c as the light emitting portion 2 in FIG. 3. Therefore, the LED light source 22 and the light shielding elastic member 25 around the LED light source 22, included in the light emitting portion 2 must be arranged so as to avoid the flexible substrate 11. Therefore, in the present embodiment, the LED light source 22 is arranged in a rectangular region 12 whose ends are sandwiched between the flexible substrates of the plurality of flexible substrates 11 when viewed from the side of the back surface 7b of the housing 7, thereby avoiding interference between components.

That is, the direction in which the intensity of the light emitted from the LED light source 22 is strongest passes between the flexible substrates.

Also in the radiation imaging apparatus 100-2 according to the second embodiment, as shown in FIG. 5, the LED light source 22 emitting light indicating the state of the radiation imaging apparatus 100 is arranged inside the outer shape obtained by projecting the radiation detection panel 3 onto the back surface 7b of the housing 7.

Third Embodiment

Next, a third embodiment of the present disclosure will be described. In the description of the third embodiment described below, the description of matters common to the first and second embodiments described above will be omitted, and matters different from the first and second embodiments described above will be described.

The schematic configuration of the radiation imaging system according to the third embodiment is the same as that of the radiation imaging system 10 according to the first embodiment shown in FIG. 1. The external appearance of the radiation imaging apparatus 100 according to the third embodiment is almost the same as that of the radiation imaging apparatus 100 according to the first embodiment shown in FIGS. 2A and 2B. Furthermore, the internal configuration of the radiation imaging apparatus 100 according to the third embodiment is almost the same as that of the radiation imaging apparatus 100 according to the first embodiment shown in FIG. 3.

Figure 8:
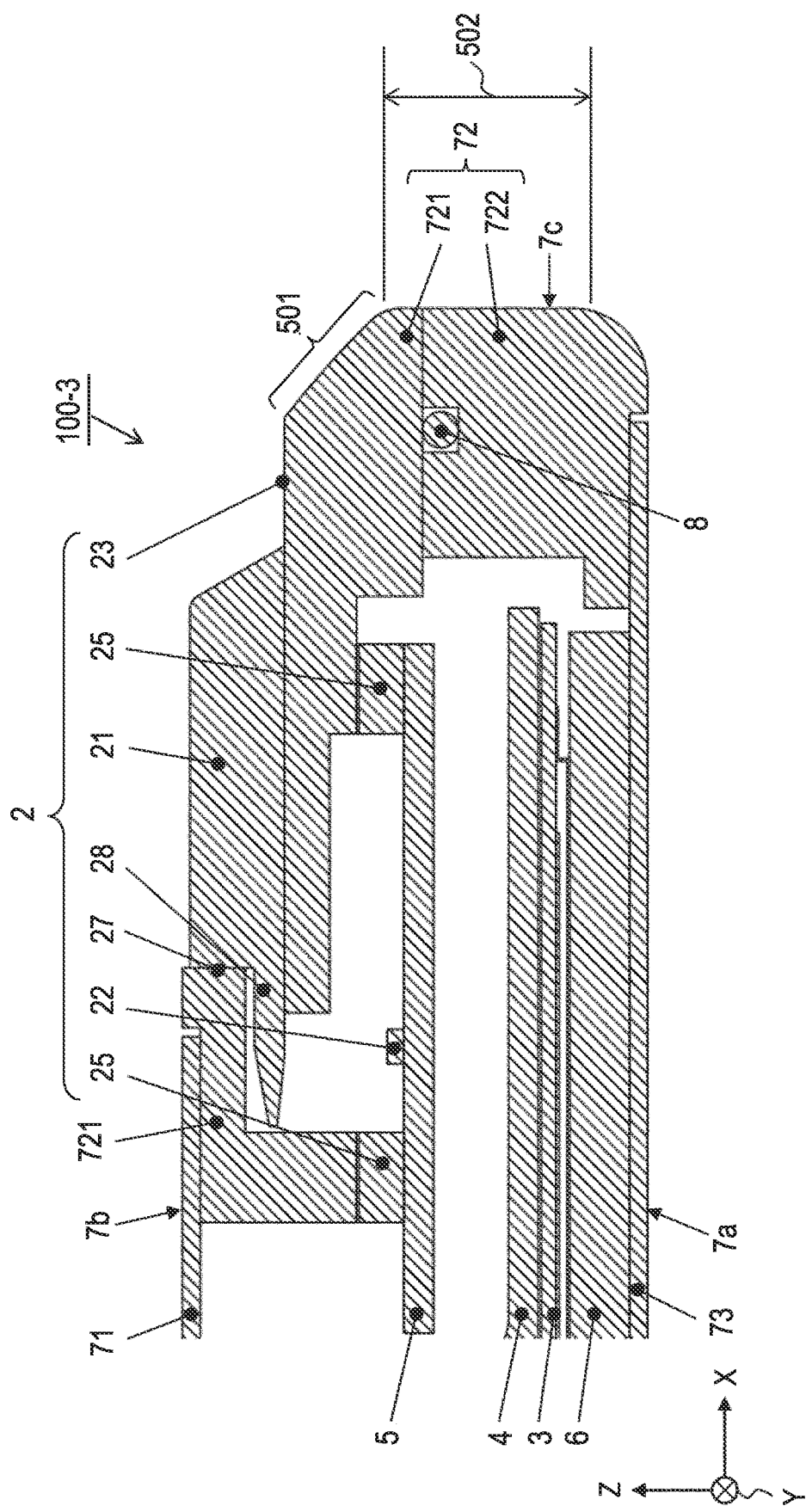
FIG. 8 is an enlarged view showing a detailed structural example of the vicinity of the light emitting portion of FIG. 3 in the radiation imaging apparatus according to the third embodiment.

FIG. 8 shows a radiation imaging apparatus 100 according to the third embodiment of the present disclosure, and shows a detailed example of a structure near the light emitting portion 2 of FIG. 3. In FIG. 8, components similar to those shown in FIGS. 3 to 5 are denoted by the same reference numerals, and a detailed description thereof will be omitted. FIG. 8 also shows an XYZ coordinate system corresponding to the XYZ coordinate system shown in FIGS. 3 to 5. In the following description, the radiation imaging apparatus 100 according to the third embodiment shown in FIG. 8 is described as "radiographic apparatus 100-3".

The light emitting portion 2 includes a light guide lens 21, an LED light source 22, a first surface 23, a light shielding elastic member 25, a second surface 27, and an opening 28.

Of these, the light guide lens 21, the LED light source 22, the first surface 23, and the light shielding elastic member 25 are the same as those of the radiation imaging apparatus 100-2 according to the second embodiment shown in FIG. 5, and therefore a detailed description thereof will be omitted. The second surface 27 is a surface substantially parallel to the side surface 7c of the housing 7 and extending to the edge in the frame 72 (back frame 721) of the housing 7 formed in a region including the side surface 7c of the housing 7, and at least a part of the region is a surface in contact with the light guide lens 21 composed of a transparent member. The opening 28 is provided in the vicinity of the second surface 27. More specifically, the opening 28 is an opening formed between the back frame 721 in contact with the front frame 722 formed on the side surface 7c and the back frame 721 in contact with the back cover 71 formed on the back surface 7b. In the radiation imaging apparatus 100-3, the light emitted from the LED light source 22 passes through the opening 28 and the light guide lens 21 and is guided toward the side surface 7c of the housing 7.

In the radiation imaging apparatus 100-3 shown in FIG. 8, the light guide lens 21 is shaped to project from the opening 28 to the inside of the housing 7. By constituting the light guide lens 21 in this way, the distance between the light guide lens 21 and the control substrate 5 becomes large. Thus, even when the housing 7 receives a load from the direction of the back surface 7b, the possibility that the light guide lens 21 damages the control substrate 5 is reduced. That is, the load resistance can be improved by this configuration.

Also in the radiation imaging apparatus 100-3 according to the third embodiment, the LED light source 22 emitting light indicating the state of the radiation imaging apparatus 100 is arranged inside the outer shape obtained by projecting the radiation detection panel 3 onto the back surface 7b of the housing 7.

Fourth Embodiment

Next, a fourth embodiment of the present disclosure will be described. In the description of the fourth embodiment described below, the description of matters common to the first to third embodiments described above will be omitted, and matters different from the first to third embodiments described above will be described.

The schematic configuration of the radiation imaging system according to the fourth embodiment is the same as that of the radiation imaging system 10 according to the first embodiment shown in FIG. 1. The external appearance of the radiation imaging apparatus 100 according to the fourth embodiment is almost the same as that of the radiation imaging apparatus 100 according to the first embodiment shown in FIGS. 2A and 2B. Furthermore, the internal configuration of the radiation imaging apparatus 100 according to the fourth embodiment is almost the same as that of the radiation imaging apparatus 100 according to the first embodiment shown in FIG. 3.

Figure 9:
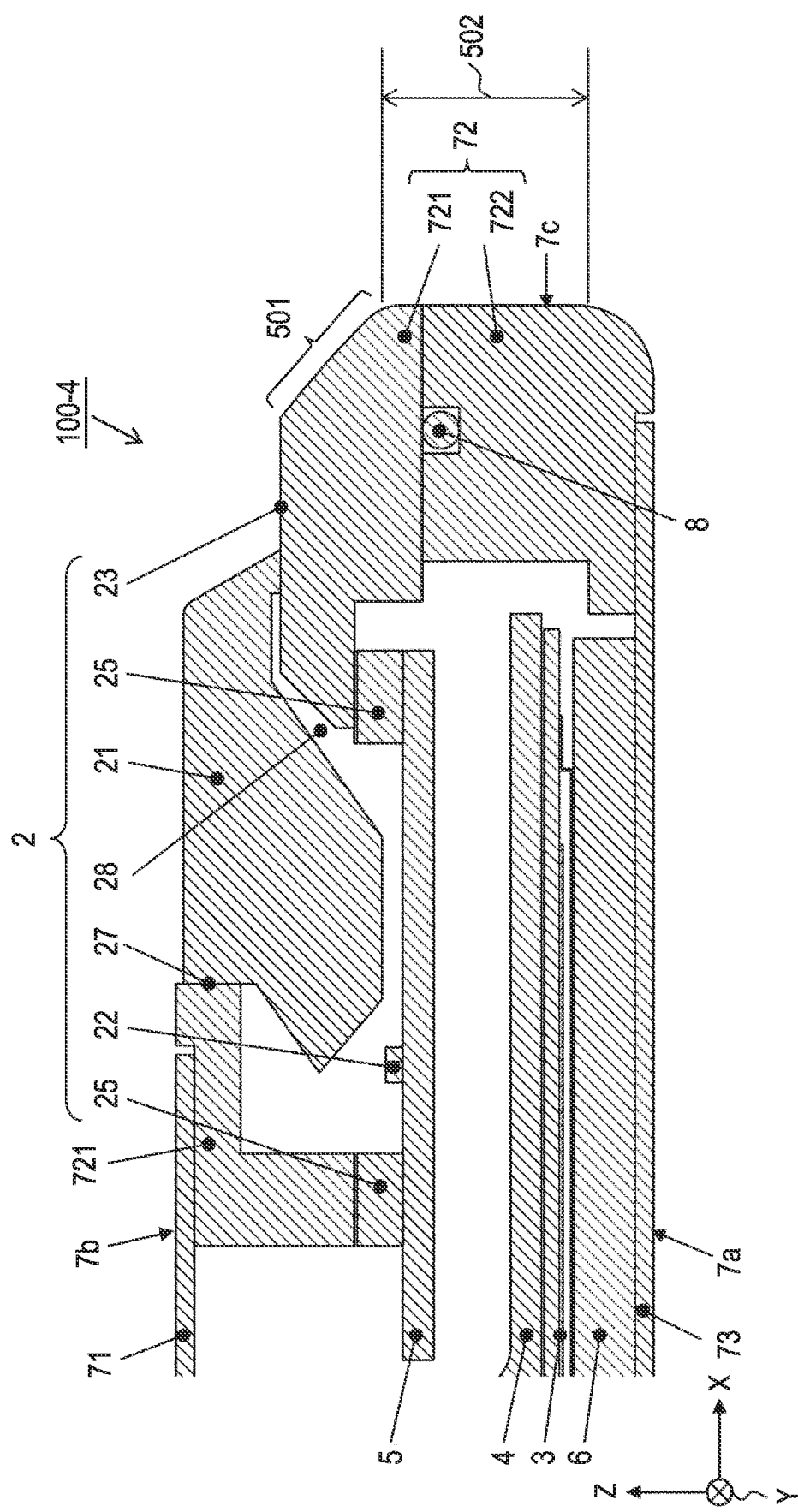
FIG. 9 is an enlarged view showing a detailed structural example of the vicinity of the light emitting portion of FIG. 3 in the radiation imaging apparatus according to the fourth embodiment.

FIG. 9 shows a radiation imaging apparatus 100 according to the fourth embodiment of the present disclosure, and shows a detailed example of the structure near the light emitting portion 2 of FIG. 3. In FIG. 9, components similar to those shown in FIGS. 3 to 5 and 8 are denoted by the same reference numerals, and detailed description thereof will be omitted. FIG. 9 also shows an XYZ coordinate system corresponding to the XYZ coordinate system shown in FIGS. 3 to 5 and 8. In the following description, the radiation imaging apparatus 100 according to the fourth embodiment shown in FIG. 9 is described as "radiographic apparatus 100-4".

In the radiation imaging apparatus 100-4, the light guide lens 21 is provided so as to span the first surface 23 and the second surface 27. The light guide lens 21 is shaped to enter the inside of the housing 7 through the opening 28. By constituting the light guide lens 21 in this way, a component incident on the light guide lens 21 in the direction angle of the light emitted from the LED light source 22 becomes large. That is, the visibility of the light emitting portion 2 can be improved by this configuration.

Also in the radiographic apparatus 100-4 according to the fourth embodiment, the LED light source 22 emitting light indicating the state of the radiation imaging apparatus 100 is arranged inside the outer shape obtained by projecting the radiation detection panel 3 onto the back surface 7b of the housing 7.

According to the present disclosure, the state of the radiation imaging apparatus can be visually confirmed while suppressing the enlargement of the frame size of the housing 7.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2021-058314, filed Mar. 30, 2021, which is hereby incorporated by reference herein in its entirety.

What is claimed is:

1. A radiation imaging apparatus comprising:
   a radiation detection panel configured to detect incident radiation and convert the incident radiation into an electric signal;
   a light source configured to emit light indicating a state of the radiation imaging apparatus;
   a housing configured to include the radiation detection panel and the light source, wherein the housing has a front surface upon which the radiation is incident, a back surface at a position opposite from the front surface, and a side surface positioned between the front surface and the back surface, wherein the housing has an opening portion and a recess portion on the back surface; and
   a transparent member configured to receive the light emitted from the light source and provided to cover the opening portion,
   wherein the light source is arranged between the radiation detection panel and the back surface,
   wherein the housing has an inclined surface connecting the side surface and the back surface, and the transparent member is located in a region on a center side of the housing more than the inclined surface, and
   wherein the light emitted from the light source is directed toward the side surface of the housing through the opening portion, the transparent member and the recess portion extended toward the side surface of the housing.

2. The radiation imaging apparatus according to claim 1, wherein the transparent member contacts a first surface substantially parallel to the back surface among surfaces forming the recess portion, and a second surface substantially parallel to the side surface among the surfaces forming the recess portion.

3. The radiation imaging apparatus according to claim 1, further comprising an electric substrate located on a side of the back surface of the housing,
   wherein the light source is located on a side of the back surface of the housing, and
   a light shielding layer, for blocking the light emitted from the light source from transmitting to a side on which the radiation detection panel is located, is formed on the electric substrate.

4. The radiation imaging apparatus according to claim 1, further comprising:
   an electric substrate located on a side of the back surface of the housing; and
   a plurality of flexible substrates connecting the electric substrate with the radiation detection panel,
   wherein the light source is located on a side of the back surface of the housing, and at least a part of the light source is located in a rectangular region sandwiched between the flexible substrates of the plurality of flexible substrates when viewed from the side of the back surface of the housing.

5. The radiation imaging apparatus according to claim 1, wherein the light emitted from the light source indicates a state of a connection with a platform or a recumbent into which the radiation imaging apparatus is inserted.

6. The radiation imaging apparatus according to claim 1, wherein the state of the radiation imaging apparatus includes a state in which the radiation imaging apparatus is inserted into a platform and can communicate with a signal processing apparatus, and a state in which the radiation imaging apparatus is inserted into the platform but cannot communicate with the signal processing apparatus.

7. A radiation imaging system comprising:
   the radiation imaging apparatus according to claim 1; and
   a radiation generator for irradiating an object with radiation,
   wherein the radiation detection panel detects the radiation transmitted through the object as an electric signal related to the radiation image.

8. A radiation imaging apparatus comprising:
   a radiation detection panel configured to detect incident radiation and convert the incident radiation into an electric signal;
   a light source configured to emit light indicating a state of the radiation imaging apparatus;
   a housing configured to include the radiation detection panel and the light source, wherein the housing has a front surface upon which the radiation is incident, a back surface at a position opposite from the front surface, and a side surface positioned between the front surface and the back surface, wherein the housing has an opening portion and a recess portion on the back surface;
   a transparent member configured to receive the light emitted from the light source and provided to cover the opening portion;
   an electric substrate located on a side of the back surface of the housing; and
   a light shielding elastic member interposed between the electric substrate and the housing,
   wherein the light source is arranged between the radiation detection panel and the back surface,
   wherein the light source is arranged in a space surrounded by the electric substrate, the light shielding elastic member, the housing, and the transparent member, and
   wherein the light emitted from the light source is directed toward the side surface of the housing through the opening portion, the transparent member and the recess portion extended toward the side surface of the housing.

9. The radiation imaging apparatus according to claim 8, wherein the light source is located on a side of the back surface of the housing, and
   a light shielding layer, for blocking the light emitted from the light source from transmitting to a side on which the radiation detection panel is located, is formed on the electric substrate.

10. The radiation imaging apparatus according to claim 8, further comprising:
    a plurality of flexible substrates connecting the electric substrate with the radiation detection panel,
    wherein the light source is located on a side of the back surface of the housing, and at least a part of the light source is located in a rectangular region sandwiched between the flexible substrates of the plurality of flexible substrates when viewed from the side of the back surface of the housing.

11. The radiation imaging apparatus according to claim 8, wherein the light emitted from the light source indicates a state of a connection with a platform or a recumbent into which the radiation imaging apparatus is inserted.

12. The radiation imaging apparatus according to claim 8, wherein the state of the radiation imaging apparatus includes a state in which the radiation imaging apparatus is inserted into a platform and can communicate with a signal processing apparatus, and a state in which the radiation imaging apparatus is inserted into the platform but cannot communicate with the signal processing apparatus.

13. A radiation imaging apparatus comprising:
    a radiation detection panel configured to detect incident radiation and convert the incident radiation into an electric signal;
    a light source configured to emit light indicating a state of the radiation imaging apparatus;
    a housing configured to include the radiation detection panel and the light source, wherein the housing has a front surface upon which the radiation is incident, a back surface at a position opposite from the front surface, and a side surface positioned between the front surface and the back surface, wherein the housing has an opening portion and a recess portion on the back surface; and
    a transparent member configured to receive the light emitted from the light source and provided to cover the opening portion,
    wherein the light source is arranged between the radiation detection panel and the back surface,
    wherein transparent member has a projection portion inserted into the housing through the opening portion, and
    wherein the light emitted from the light source is directed toward the side surface of the housing through the opening portion, the transparent member and the recess portion extended toward the side surface of the housing.

14. The radiation imaging apparatus according to claim 13, wherein the projection portion has a light receiving surface facing the light source and receiving the light emitted from the light source, and a reflecting surface opposed to the light receiving surface and reflecting light arriving from the light receiving surface, and
    wherein at least one of the light receiving surface and the reflecting surface has a shape recessed inward of the transparent member.

15. The radiation imaging apparatus according to claim 13, further comprising an electric substrate located on a side of the back surface of the housing, wherein the light source is located on a side of the back surface of the housing, and a light shielding layer, for blocking the light emitted from the light source from transmitting to a side on which the radiation detection panel is located, is formed on the electric substrate.

16. The radiation imaging apparatus according to claim 13, further comprising:

an electric substrate located on a side of the back surface of the housing; and a plurality of flexible substrates connecting the electric substrate with the radiation detection panel, wherein the light source is located on a side of the back surface of the housing, and at least a part of the light source is located in a rectangular region sandwiched between the flexible substrates of the plurality of flexible substrates when viewed from the side of the back surface of the housing.

17. The radiation imaging apparatus according to claim 13, wherein the light emitted from the light source indicates a state of a connection with a platform or a recumbent into which the radiation imaging apparatus is inserted.

18. The radiation imaging apparatus according to claim 13, wherein the state of the radiation imaging apparatus includes a state in which the radiation imaging apparatus is inserted into a platform and can communicate with a signal processing apparatus, and a state in which the radiation imaging apparatus is inserted into the platform but cannot communicate with the signal processing apparatus.

19. The radiation imaging apparatus according to claim 14, wherein the light receiving surface of the transparent member has an arc shape, and the radius of the arc shape is smaller than a distance between the light receiving surface and the light source.

\* \* \* \* \*